United States Patent
Seetharam et al.

(10) Patent No.: US 11,804,305 B2
(45) Date of Patent: Oct. 31, 2023

(54) CONTRALATERAL IMAGE ORTHOPEDIC IMPLANT

(71) Applicant: Orthopedix, Inc., Providence, RI (US)

(72) Inventors: Ashok Seetharam, Providence, RI (US); Adam E. Eltorai, Marlborough, MA (US); Vishal J. Thomas, Louisville, KY (US)

(73) Assignee: Mosaic Ventures, LLC, Marlborough, MA (US)

(*) Notice: Subject to any disclaimer, the term of this patent is extended or adjusted under 35 U.S.C. 154(b) by 302 days.

(21) Appl. No.: 15/412,458

(22) Filed: Jan. 23, 2017

(65) Prior Publication Data
US 2018/0113992 A1    Apr. 26, 2018

Related U.S. Application Data

(60) Provisional application No. 62/412,836, filed on Oct. 26, 2016.

(51) Int. Cl.
*G16H 30/40* (2018.01)
*G16H 50/50* (2018.01)
(Continued)

(52) U.S. Cl.
CPC ......... *G16H 50/50* (2018.01); *A61F 2/30942* (2013.01); *A61F 2/4261* (2013.01);
(Continued)

(58) Field of Classification Search
CPC .. G06Q 50/22–24; G16H 50/50; G16H 30/40; G06F 30/00; A61F 2/30942;
(Continued)

(56) References Cited

U.S. PATENT DOCUMENTS 5,705,117 A * 1/1998 O'Connor ............... B29C 41/20
264/401
5,787,889 A * 8/1998 Edwards ............. G01S 15/8993
128/916
(Continued)

FOREIGN PATENT DOCUMENTS

CN       204448783 U    9/2016
WO    2010151589 A1   12/2010
(Continued)

OTHER PUBLICATIONS

Black, C. R., Goriainov, V., Gibbs, D., Kanczler, J., Tare, R. S., & Oreffo, R. O. (2015). Bone Tissue Engineering. Current molecular biology reports, 1(3), 132-140. (Year: 2015).*

*Primary Examiner* — Joshua B Blanchette
*Assistant Examiner* — Winston Furtado
(74) *Attorney, Agent, or Firm* — Armis IP Law, LLC (57) ABSTRACT

A fabrication system and method for prosthetic appliances employs imaging of a contralateral skeletal structure for designing a matched, patient specific replacement appliance based on the patient's own skeletal structure. Many skeletal structures are disposed on opposed sides, i.e. left and right sides. A contralateral bone or skeletal member often accurately depicts the individual bone shape of a particular patient more accurately than a generalized approximation. A scan such as a CT or MRI is segmented to apportion a skeletal member for replacement and reconstructed into a 3D (3 dimensional) model. The 3D model is inverted to define the contralateral side, and augmented for surgical connection features and comparison with an anatomic ideal to mitigate imperfections. 3D printing and/or additive manufacturing techniques are invoked with biocompatible materials to render the replacement prosthetic appliance based on the model.

12 Claims, 7 Drawing Sheets

(51) Int. Cl.
*G06F 30/00* (2020.01)
*H04N 1/00* (2006.01)
*A61F 2/30* (2006.01)
*A61F 2/42* (2006.01)
*B33Y 50/02* (2015.01)
*B33Y 10/00* (2015.01)
*B33Y 80/00* (2015.01)

(52) U.S. Cl.
CPC ............. *G06F 30/00* (2020.01); *G16H 30/40* (2018.01); *H04N 1/00* (2013.01); *A61F 2002/30948* (2013.01); *A61F 2002/30952* (2013.01); *A61F 2002/30962* (2013.01); *A61F 2240/002* (2013.01); *B33Y 10/00* (2014.12); *B33Y 50/02* (2014.12); *B33Y 80/00* (2014.12)

(58) Field of Classification Search
CPC .......... A61F 2/4261; A61F 2002/30948; A61F 2002/30952; A61F 2002/30962; A61F 2240/002; H04N 1/00; B33Y 10/00; B33Y 50/02; B33Y 80/00
USPC ............................................................. 705/2
See application file for complete search history.

(56) References Cited

U.S. PATENT DOCUMENTS

| | | | |
|---|---|---|---|
| 7,603,192 B2 * | 10/2009 | Martin | A61B 17/8061 700/98 |
| 7,747,305 B2 * | 6/2010 | Dean | A61F 2/30942 600/407 |
| 7,837,739 B2 | 11/2010 | Ogilvie | |
| 8,457,930 B2 * | 6/2013 | Schroeder | A61F 2/30 703/1 |
| 8,579,620 B2 * | 11/2013 | Wu | G06T 17/00 425/7 |
| 8,709,089 B2 | 4/2014 | Lang et al. | |
| 8,843,229 B2 | 9/2014 | Vanasse et al. | |
| 9,119,613 B2 | 9/2015 | Gannoe | |
| 2008/0182220 A1 * | 7/2008 | Chishti | A61C 7/00 433/24 |
| 2010/0292963 A1 * | 11/2010 | Schroeder | G16H 50/50 703/1 |
| 2011/0004317 A1 * | 1/2011 | Hacking | A61F 2/4261 600/416 |
| 2014/0025181 A1 | 1/2014 | Vanasse et al. | |
| 2014/0228860 A1 * | 8/2014 | Steines | A61B 34/30 606/130 |
| 2014/0371863 A1 | 12/2014 | Vanasse et al. | |
| 2017/0360578 A1 * | 12/2017 | Shin | G09B 23/286 |
| 2018/0113992 A1 * | 4/2018 | Eltorai | G06F 17/50 |

FOREIGN PATENT DOCUMENTS

WO WO-2011028624 A1 * 3/2011 ........... A61B 17/155
WO 2014014610 A1 1/2014

* cited by examiner

CONTRALATERAL IMAGE ORTHOPEDIC IMPLANT

RELATED APPLICATIONS

This application claims the benefit under 35 U.S.C. § 119(e) of U.S. Provisional Patent Application No. 62/412,836, filed Oct. 26, 2016, entitled "METHOD OF CREATING PATIENT-SPECIFIC IMPLANTS USING CONTRALATERAL RADIOGRAPHIC IMAGES TO RECONSTRUCT PRE-DISEASE ANATOMICAL SHAPE," incorporated herein by reference in entirety.

BACKGROUND

Prosthetic appliances are surgical implants that replace natural skeletal structures in a patient, and include orthopedic implants which replace and/or support a natural bone in a patient. Natural skeletal structures such as bones, tendons and ligaments can be compromised by age, disease and traumatic injury, as well as other causes. Surgical replacement with an orthopedic implant attempts to duplicate the original bone or skeletal member so that the patient may continue to enjoy mobility and dexterity once provided by healthy skeletal members. Replacement orthopedic implants are particularly beneficial in the wrist, ankle, and related digit members, as the natural skeletal structures include an arrangement of small, interconnected bones having specific irregular shapes that mesh and cooperate with other adjacent bones. Precise fabrication of these complex shapes using expensive and unwieldy metals such as titanium is often employed for reliable implants.

SUMMARY

A fabrication system and method for prosthetic appliances employs imaging of a contralateral skeletal structure for designing a matched, patient specific replacement appliance based on the patient's own skeletal structure, rather than a mass-produced generalization of common bone structure. Many skeletal structures are disposed on opposed sides, i.e. left and right sides. A contralateral bone or skeletal member often accurately depicts the individual bone shape of a particular patient more so than a generalized approximation. Since the contralateral structures are reversed, or "mirror images" of each other, configurations herein transpose and interpolate a structure from a healthy side scan to better approximate the replacement appliance for the unhealthy side. A scan such as a 2D (2 dimensional) CT or MRI is segmented to apportion a skeletal member for replacement and reconstructed into a 3D (3 dimensional) model. The 3D model is inverted to define the contralateral (unhealthy) side, and augmented for connection features and comparison with an anatomic ideal to mitigate imperfections. 3D printing and/or additive manufacturing techniques are invoked with biocompatible materials to render the replacement prosthetic appliance based on the model.

Configurations herein are based, in part, on the observation that orthopedic implants attempt to accurately replicate native skeletal bone members to restore as much dexterity and mobility as possible, and reduce or eliminate pain or discomfort in movement. Unfortunately, conventional approaches for orthopedic implant replacement suffer from the shortcoming that the surgical replacement exhibits deviation in size and shape from the bone they replace, which imparts changes in tolerance, spacing and fit between adjacent bone members in an integrated network of cooperative structures. Such deviations, while permitting enhanced movement over the diseased member they replace, nonetheless may fall short of the fully functioning healthy native bone. Accordingly, configurations herein employ contralateral imaging and CAD/CAM manufacturing to construct an orthopedic implant based on the native bone structure to more accurately reproduce the healthy skeletal member they replace. Natural anatomical deviations from patient to patient make it difficult to develop a universal model for all patients. The disclosed patient specific model and 3D printing/additive manufacturing fabrication provides a replacement skeletal member derived from the patient's own physical characteristics.

Orthopedic wrist implants as disclosed herein, for example, are expected to benefit a diverse array of patients, most notably patients suffering from thumb CMC arthritis, Kienbock's disease and scaphoid non-union fracture, none of which have proven and long lasting treatments, can have a perfect replacement of the damaged bone designed specifically for the damaged region. Such precision and conformity translates to a better perceived fit, shorter recovery time and improved osteo-integration. Surgeons benefit in the way of reduced infection risks and higher satisfaction among their patients. Hospitals have the benefit of reduced inventory costs, higher throughput and an availability of implants on demand.

In the cases of damage or fracture on the trapezium, lunate or scaphoid bones, contralateral images of the corresponding healthy bones are taken. The 2D images are segmented as required and then reconstructed to 3D models which are post-processed using 3D modeling software. This post-processed model is then used to design the implant. Now, the implant geometries can be difficult to duplicate through conventional manufacturing methods. Hence additive manufacturing is employed to obtain the requisite geometric features. Such implants are substantially identical to the wrist bones that they replace, are bio-compatible and have excellent osteo-integration. They are expected to provide a much better patient fit and feel more natural.

In further detail, the disclosed approach includes identifying a compromised skeletal structure, and receiving a scan of a contralateral anatomical structure corresponding to the compromised skeletal structure by scanning the opposite patient side for the corresponding healthy bone. A modeling and/or CAD system inverts the received scan to form a model for replacement of the compromised skeletal structure, and generates, based on the model and an anatomical ideal of the compromised skeletal structure, a replacement image of a prosthetic appliance. 3D printing is employed for fabricating a prosthetic appliance using a biocompatible material from additive manufacturing based on the replacement image.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
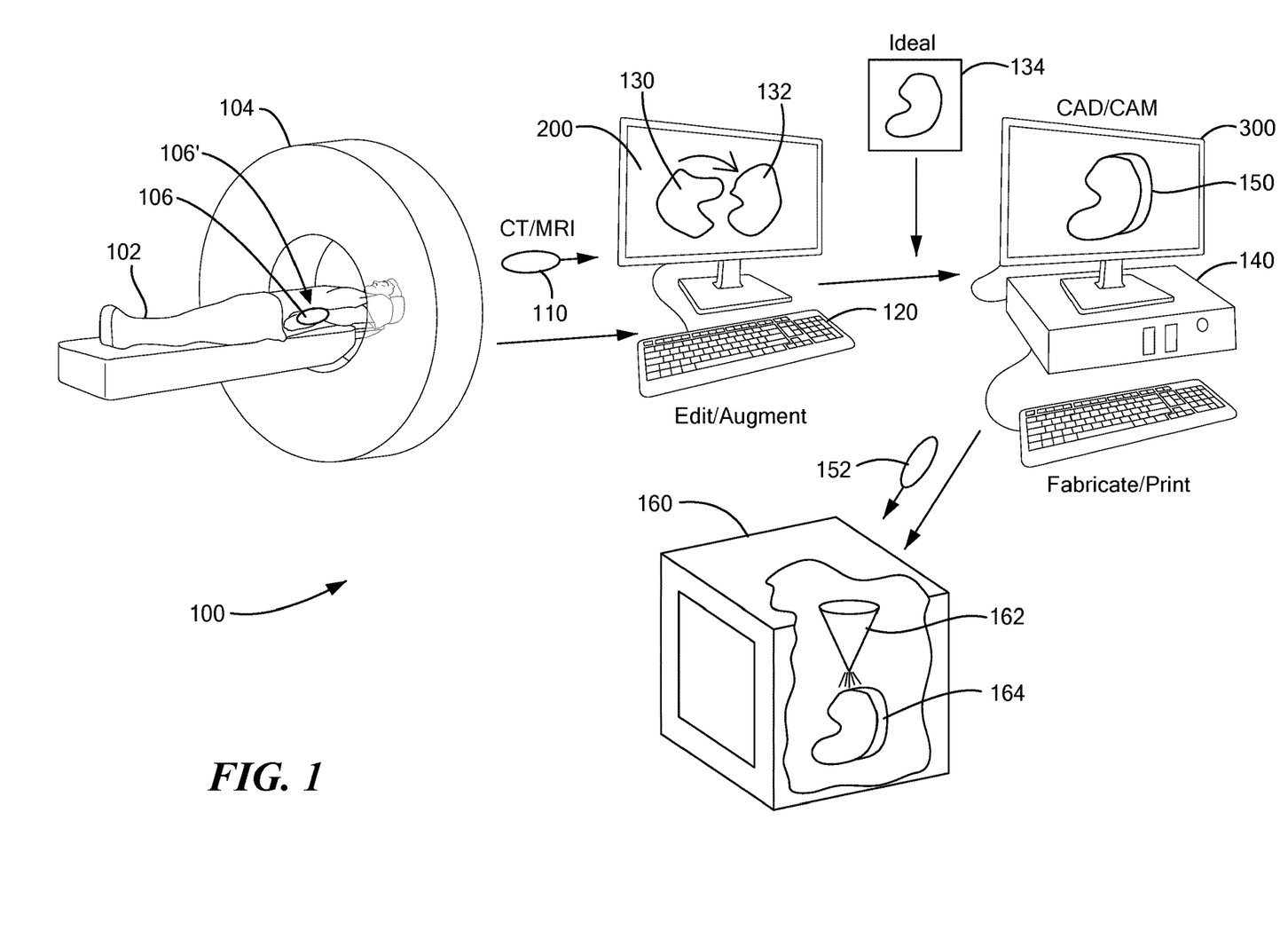
FIG. 1 is a context diagram of an orthopedic environment suitable for use with configurations herein.

Configurations below depict an example orthopedic environment for scanning and modeling orthopedic implants for surgical replacement of wrist bones. Wrist bones, in particular, benefit from the precision of the disclosed approach due to the close proximity and narrow tolerances between these skeletal structures. In contrast, more unitary skeletal members such as elongated leg or arm bones have more relaxed tolerance restrictions for maintaining adequate performance. Particular structures include the trapezium, lunate or scaphoid bones, however the disclosed approach is applicable for reproduction of any suitable contralateral arrangement of skeletal members, where a reliable approximation is obtainable from the corresponding structure on the opposed side. In the discussion that follows, the terms model, image and scan all refer to dimensional data representative of a skeletal model and manipulatable and renderable by a computer FIG. 1 is a context diagram of an orthopedic environment suitable for use with configurations herein. In the orthopedic environment 100, scan data 110 is received from a patient 102 via a scan device 104 such as a Computerized Axial Tomography (CT or CAT) scan or Magnetic Resonance Imaging (MRI) scan device. The device 104 generates scan data 110 of the contralateral structure 106 of the skeletal structure for replacement 106'. The scan data 110 is typically a series of 2-Dimensional (2D) consecutive cross-sections ("slices") received by a modeling system 120. The modeling system 120 converts the 2D images to a 3D scan or structure 130, and transposes or inverts the structure 130 to a reversed structure 132 representative of the native skeletal member to be surgically replaced. The reversed structure 132, or model is passed to a CAD/CAM application 140. Surgical attachment points such as screw holes and suture passages are added, and comparison with an anatomical ideal 134 is performed to identify and correct blatant or apparent defects from the "healthy" scan. The modeling system 120 and CAD/CAM application 140 are generally expected to be computer software and high-resolution rendering hardware (monitors), and may be fulfilled by the same hardware base. The modeling system 120 builds a 3D contralateral model of the afflicted area, for example, as a DICOM (Digital Imaging and Communications in Medicine) file, and the CAD/CAM system 140 generates a renderable file for fabricating the prosthetic appliance on a 3D printer, such as an stl (stereolithography) file. A model 150 is generated from the surgical attachments and anatomical corrections, and a renderable structure 152 passed to a 3D printer/additive manufacturing facility 160. The 3D printer 160 is equipped with a biocompatible extrusion 162 responsive to the renderable structure to fabricate the prosthetic appliance 164.

Figure 2:
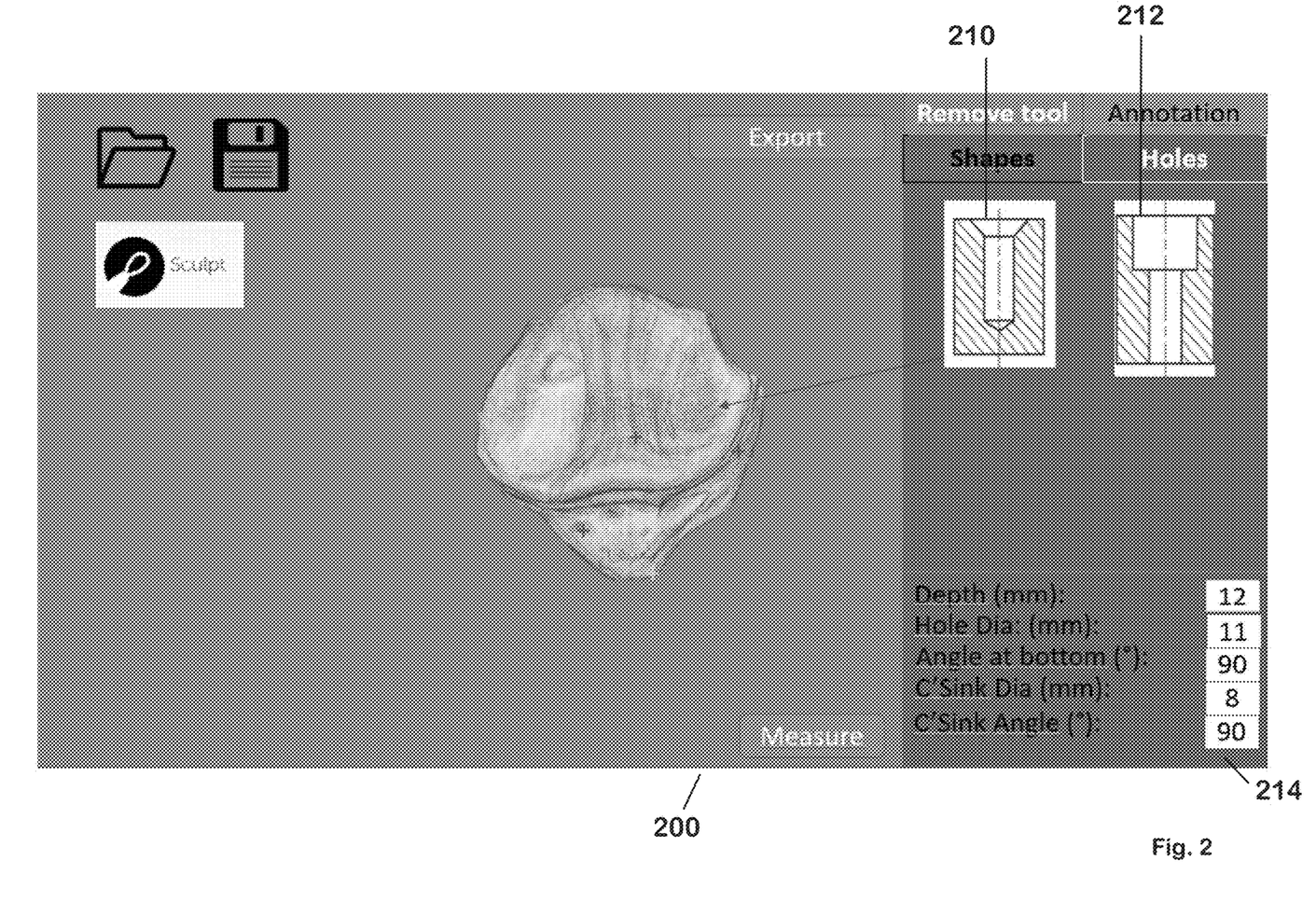
FIG. 2 is a depiction of a screen interface for adding attachment apertures and protrusions to an orthopedic appliance in the environment of FIG. 1.

FIG. 2 is a depiction of a screen interface 200 for adding attachment apertures and protrusions to an orthopedic appliance in the environment of FIG. 1. Referring to FIGS. 1 and 2, the modeling system 120 receives the scan data 110 as a series of 2D images of the contralateral anatomical structure. For example, if the patient is suffering from an arthritic left trapezium, the scan data 110 is of the right trapezium.

The modeling system 120 receives the scan data and computes a 3D model including structural enhancements to the prosthetic appliance for facilitating surgical implantation. These augmentations may be provided from input of patient specific data, surgical guidelines of typical procedures, and parameters relating to attachment mechanisms, and may be from automated or direct manual input. Receiving the scan of the contralateral anatomical structure therefore further includes analyzing a series of 2-dimensional (2D) scans of the contralateral anatomic structure, and reconstructing the 2D scans into a 3-dimensional (3D) image defining the reversed (contralateral) structure 132. Attachment features such as screw holes 210 and suture apertures 212 may be defined in the structure 132. Feature parameters 214 such as diameter and depth may be defined per surgical parameters to aid surgical attachment.

The modeling system 120 post-processes the 3D image data into a 3D model defining a replacement for the compromised skeletal structure. The modeling system 120 generates the 3D model by segmenting the series of 2D scans to extract portions of the contralateral anatomic structure and omit adjacent anatomic features from the fabricated prosthetic appliance. This extracts only the ailing skeletal feature and omits surrounding connective tissue to form a model 130 of only the skeletal structure for replacement. The modeling system transposes and interpolates the 3D image of the contralateral anatomic structure to invert the 3D image to correspond to the compromised skeletal structure on an opposed side. This reversed, or inverted structure 132 becomes the basis for the new prosthetic implant 164.

Figure 3:
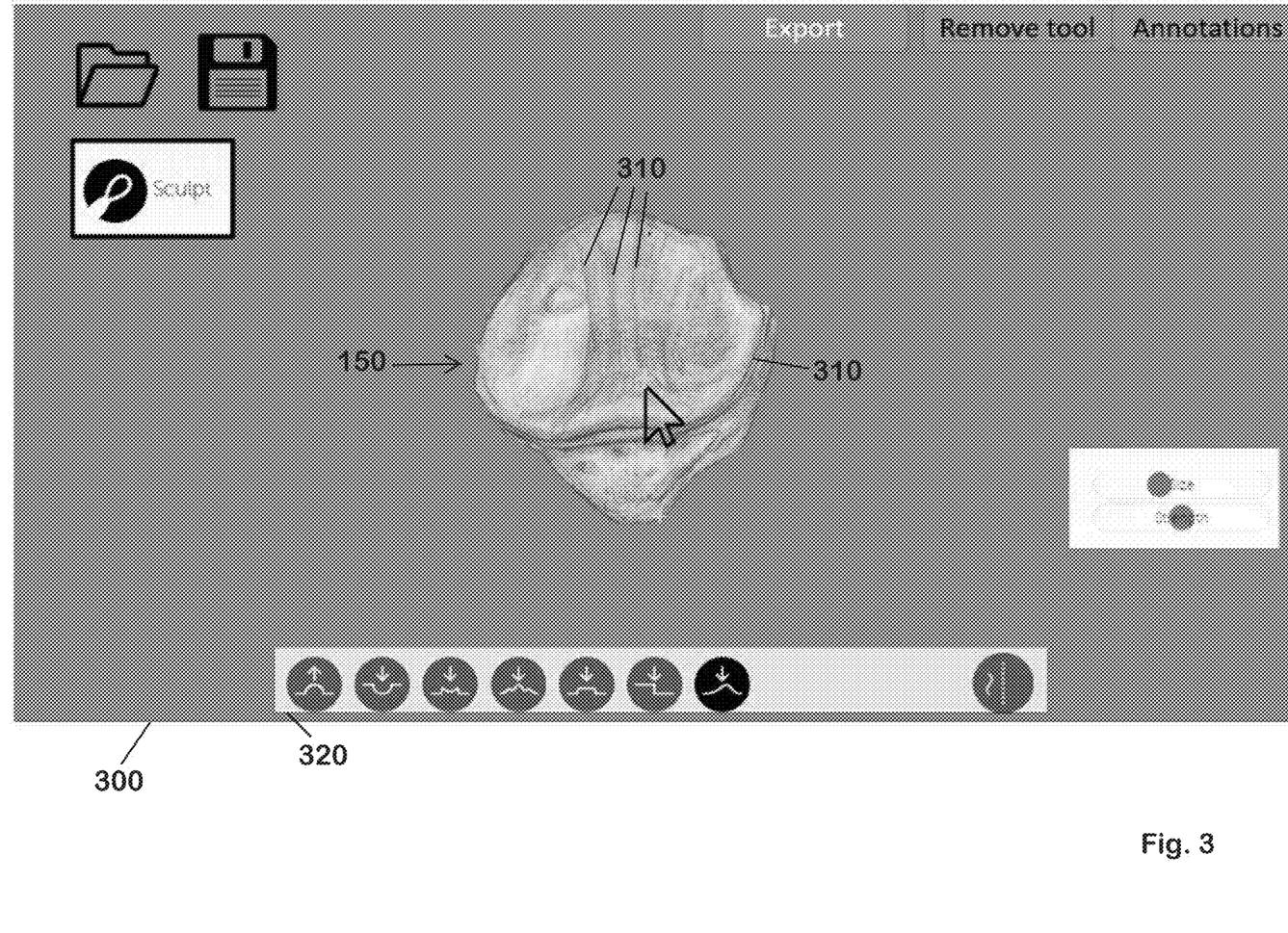
FIG. 3 is a depiction of a screen interface for adding therapeutic augmentations based on an anatomic ideal to the orthopedic appliance of FIG. 2.

FIG. 3 is a depiction of a screen interface 300 for adding therapeutic augmentations based on an anatomic ideal to the orthopedic appliance of FIG. 2. The contralateral scan data 110 may still include imperfections and deficiencies that occur in the "healthy" side structure. It is beneficial to augment the model 132 to accommodate apparent imperfections such as arthritis, fractures and necrosis. An anatomic ideal 134 is used for comparison to the structure 132, to augment the structure and generate the finished model 150. Comparisons are made by identifying corresponding ridges and edges 310 between the anatomic ideal 134 and the current structure 132 depicting the model 150. This includes receiving features of the anatomic ideal 134, the features including volumetric, surface and landmark features, and comparing the features to corresponding features depicted in the 3D model of the compromised skeletal structure. The CAD/CAM system 140 may then be used to augment the 3D model of the compromised skeletal structure based on deviations in the compared features. Features such as the ridges and edges 310 are identified and compared, and sculpting or replacement operations 320 invoked to manipulate the model 150 into the desired finished configuration. Manipulations to the model 150 include input based on observation, feature detection and automated recognition between the anatomic ideal 134 and the structure 132, for computing the location of deficiencies including arthritis, fractures and necrosis in the compromised skeletal structure.

The CAD manipulation of the model 150 may be performed by any suitable mechanism for receiving the information pertaining to surgical and clinical augmentations. Such manipulations may include the following sculpting operations for freely modifying the geometry of the model 150. Surfaces may be pulled/pushed with different intensity, erased, smoothed to decrease polygons and simplify rendering, flattened, and edged along grooves on any part of the model.

Figure 4:
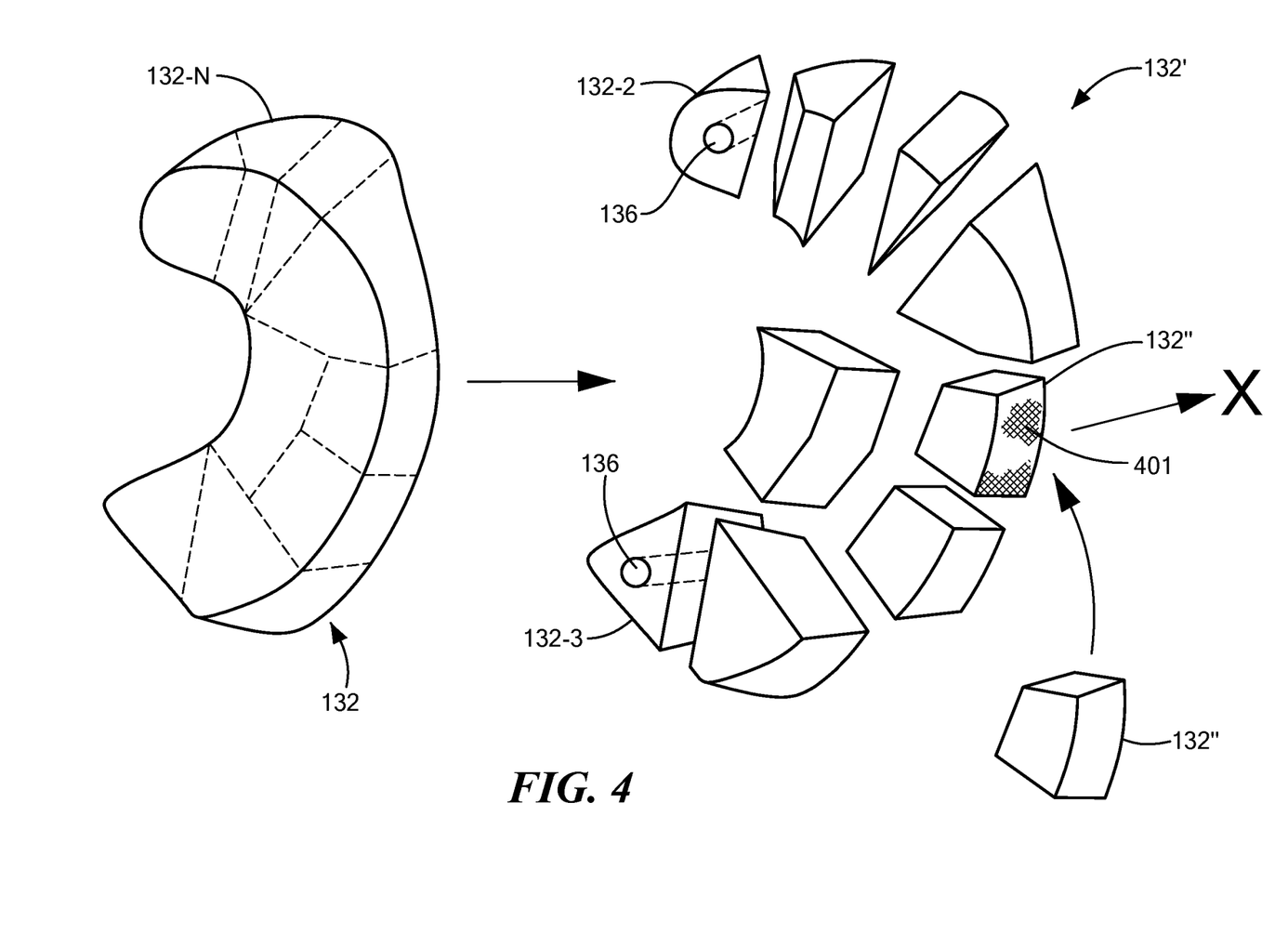
FIG. 4 shows portions of the implant for augmentation or modification using the interface of FIGS. 2 and 3.

FIG. 4 shows portions of the implant for augmentation or modification using the interface of FIGS. 2 and 3. Referring to FIGS. 2, 3 and 4, the structure 130 depicting the replacement prosthetic appliance 164 may exhibit imperfections 401 such as arthritis, fractures and necrosis. Augmentation typically includes identifying a solid homogenous bone structure as the compromised skeletal structure, such as the trapezium, lunate, scaphoid or other solid bone structure suitable for fabrication as a solid object.

Development of the model 150 for rendering based on the scanned, transposed structure 132 may include replacing portions 132-N of the structure with shapes 132" of similar size and surface. This may include identifying corresponding surfaces between the anatomic ideal 134 and the model 150, and identifying surface aberrations in the model corresponding to deficiencies in the contralateral anatomical structure that should not be transferred to the fabricated prosthetic appliance. The identified aberrations 132' are then omitted and replaced with alternative portion shapes 132" for the fabricated prosthetic appliance 164.

The CAD system 140 decomposes the solid homogeneous bone structure into a series of contiguous spatial segments 132 defining the compromised skeletal structure. For each of the contiguous spatial segments 132, a selection of a corresponding spatial segment from either the contralateral scan 130 or the anatomic ideal 134 is made, and the selected spatial segments 132" are assembled into the replacement structure 132 or model 150.

Other augmentations may include portions 132-2, 132-3 with suture apertures 136. Various augmentations may be performed using the modeling system 120 and CAD system 140, discussed in further detail in claim 5 below.

Figure 5:
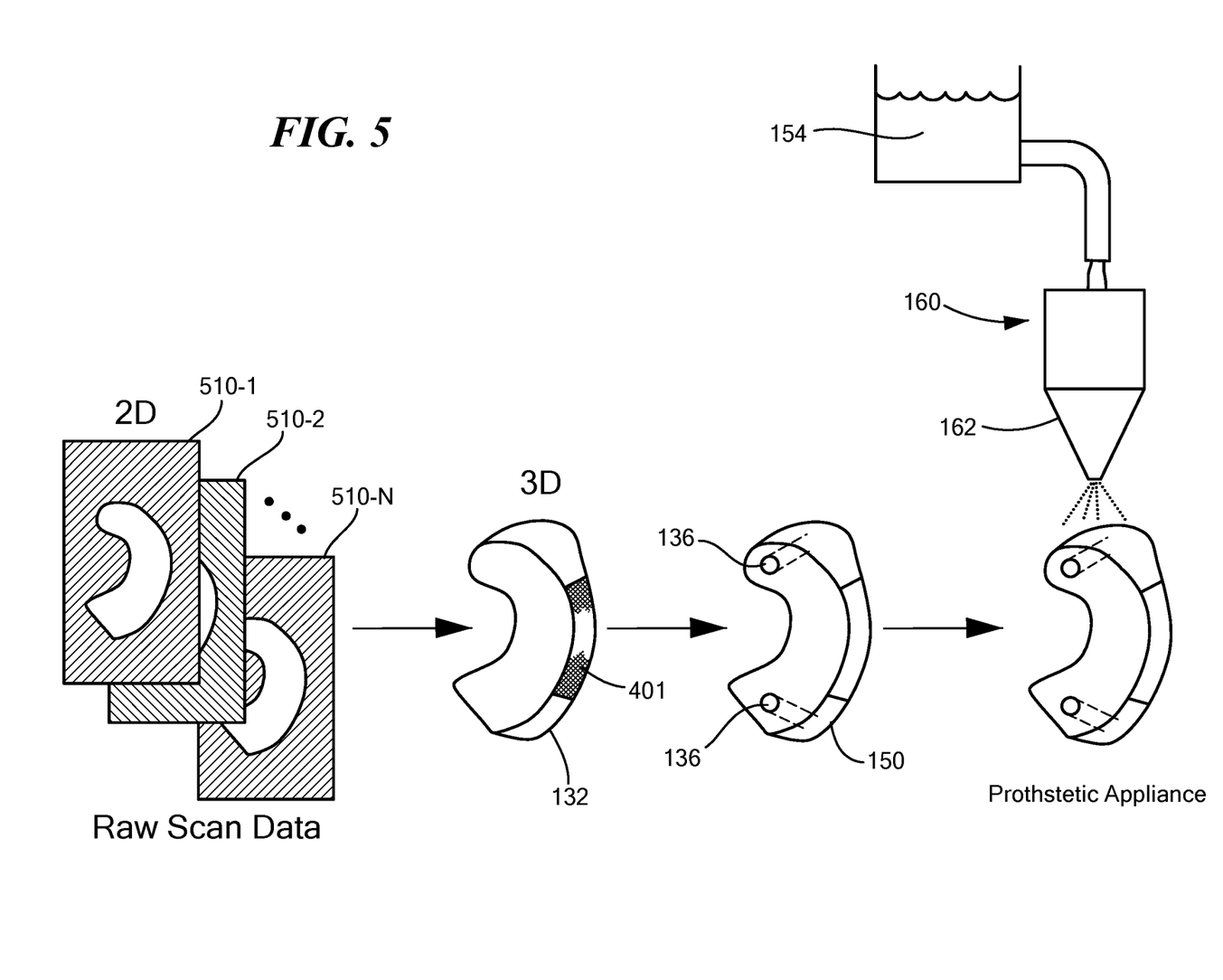
FIG. 5 is a data and manufacturing flow depicting fabrication of a prosthetic orthopedic implant in the environment of FIG. 1.

FIG. 5 is a manufacturing and data flow of an orthopedic appliance fabricated in the environment of FIG. 1. Referring to FIGS. 1 and 5, the scan data 110 is received from the CT/MRI device 104 in the form of a series of 2D images 510-1 . . . 510-N (510 generally). The modeling system 120 performs conversion, segmentation, post-processing and interpolation on the 2D images 510 to generate the 3D structure 132. The CAD system 140 receives this 3D structure and augments to accommodate imperfections and surgical structures resulting in the model 150. The model 150 is rendered (printed) by the extruder 162 in the 3D printer 160 using a biocompatible material 154 suitable for 3D printing and additive manufacturing.

Figure 6A:
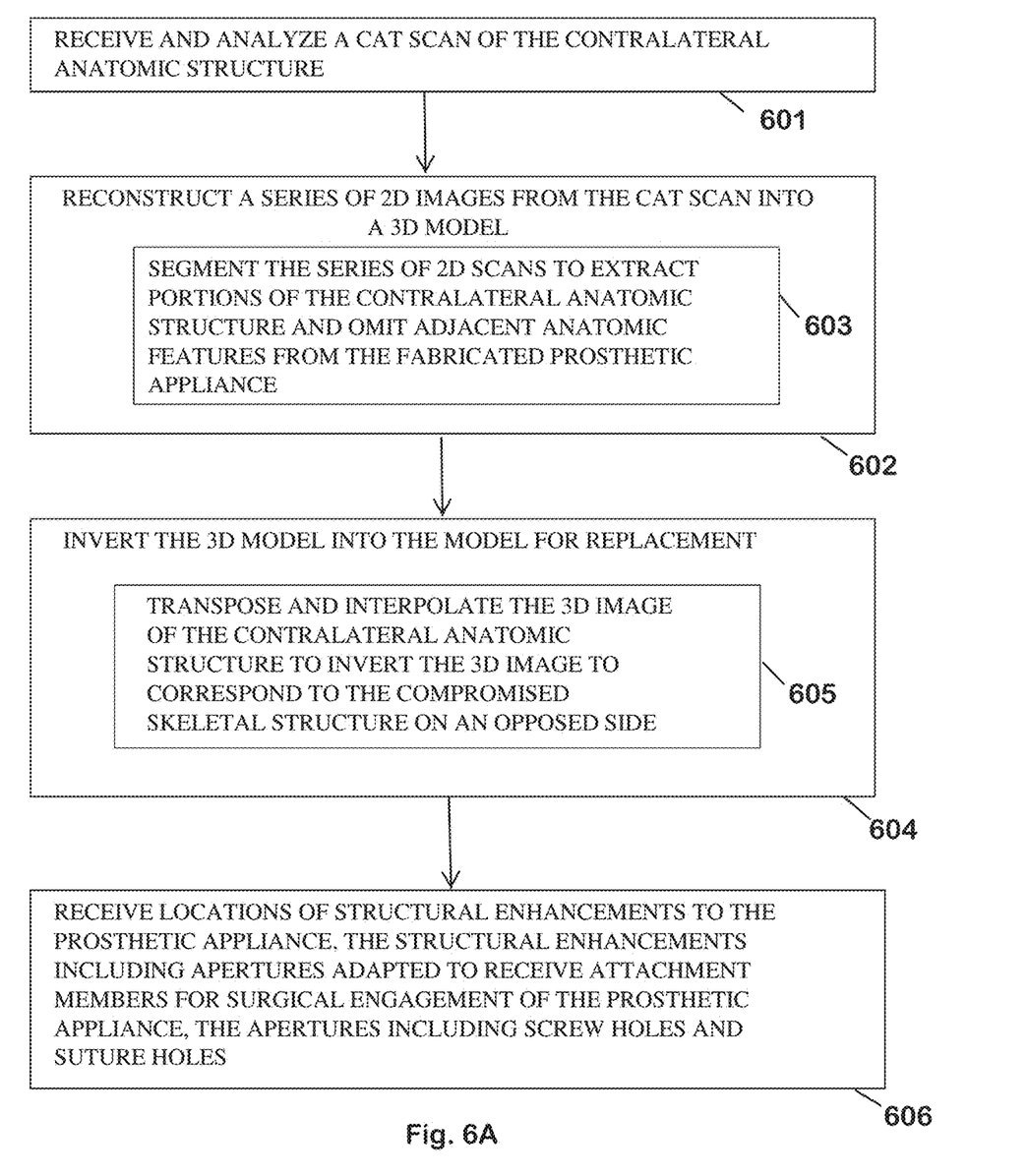
FIGS. 6A and 6B are a flowchart of the fabrication of FIG. 5.
Figure 6B:
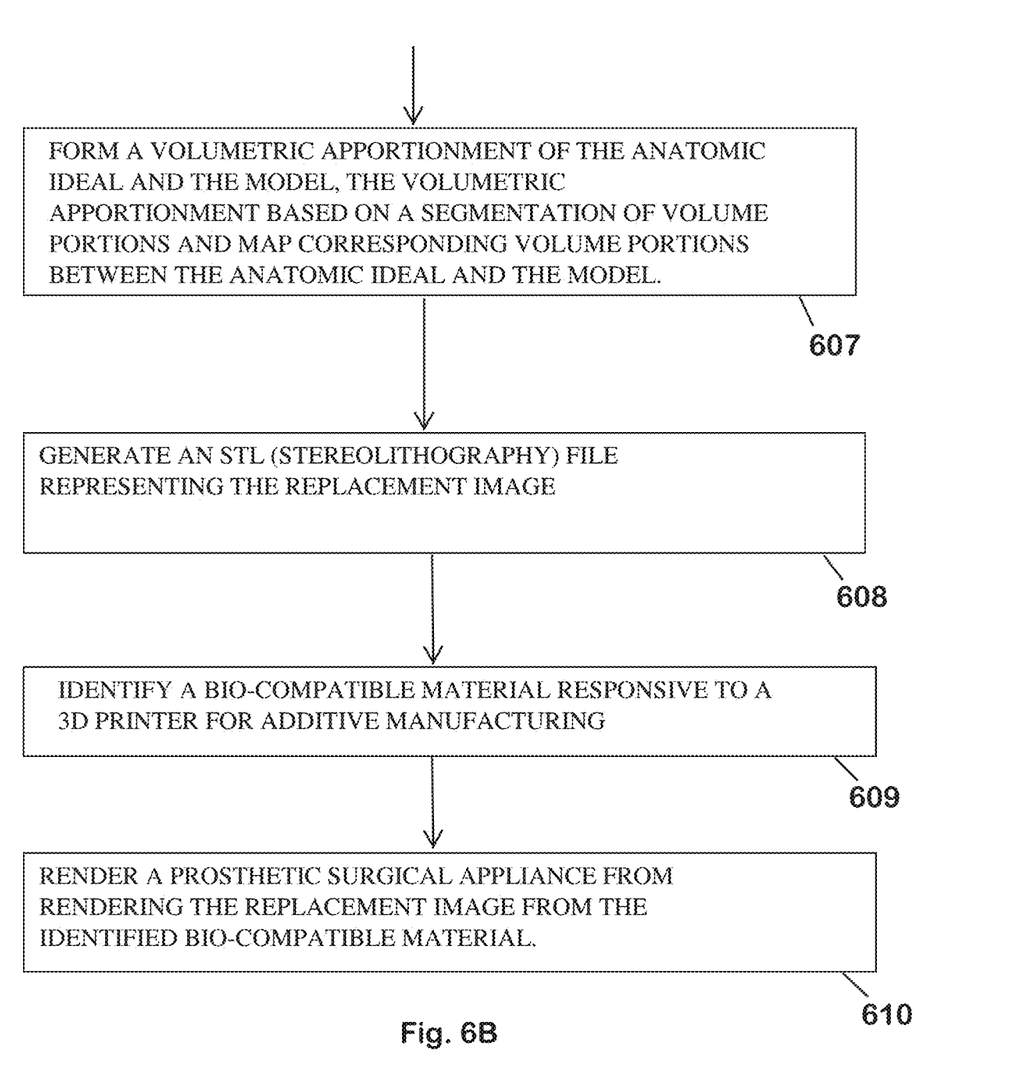

FIGS. 6A and 6B are a flowchart of the fabrication of FIG. 5. FIGS. 6A and 6B depict a particular configuration including modeling and CAD software suites for fabrication. Other systems and platforms may be utilized for performing the disclosed operations, and the various data items pertaining to scan data, anatomic ideals and augmentation may emanate from various sources, including image recognition, knowledge base response, archived images, and manual input. Referring to FIGS. 1, 4, 5, 6A and 6B, at step 601, the modeling system 120 analyzes a CAT (computerized axial tomography) scan of the contralateral anatomic structure 106. DICOM (Digital Imaging and Communications in Medicine) files are obtained from the CT/MRI scan data 110. These files include of a stack of 2D images pertaining to the patient's anatomy from the healthy joint (mirror image of the diseased side)

The modeling system reconstructs a series of 2D images from the CAT scan into a 3D model, as depicted at step 602. The stacks of images are subject to image segmentation. Open-source DICOM software (slicer and others) may be employed to convert the 2D scan data model into 3D structure 130. The resulting contours can be used to create the requisite 3D model. The modeling system 120 segments the series of 2D scans to extract portions of the contralateral anatomic structure and omit adjacent anatomic features from the fabricated prosthetic appliance, as depicted at step 603. The 3D structure (model) is post-processed, and the required bone feature is to be segmented. Segmentation is process of extracting the desired portion of the model from the entire 3D model. The segmented file is then saved as a .stl file for further design process. Alternate file formats may be employed.

At step 604, the modeling system 120 inverts the 3D structure 130 into the structure 132 for replacement. In order to get the mirror image of the healthy bone, the segmented model is then transposed and interpolated to serve as the base model of the implant which replaces the diseased bone. This involves transposing and interpolating the 3D image of the contralateral anatomic structure to invert the 3D image to correspond to the compromised skeletal structure on an opposed side, as shown at step 605.

Surgical and clinical augmentations may be needed to facilitate implantation and avoid propagating deficiencies from the scan. This includes receiving locations of structural enhancements to the prosthetic appliance 164. The structural enhancements include apertures adapted to receive attachment members for surgical engagement of the prosthetic appliance, in which the apertures may include screw holes and suture holes, as depicted at step 606. Thus, any required design modifications are made to the model (such as subtraction and other operations) in order to define the implant. This may include receiving locations of structural enhancements to the prosthetic appliance, the structural enhancements including apertures adapted to receive attachment members for surgical engagement of the prosthetic appliance.

Imperfections and deficiencies are mitigated by forming a volumetric apportionment of the anatomic ideal and the model, such that the volumetric apportionment is based on a segmentation of volume portions as in FIG. 4. Corresponding volume portions are mapped between the anatomic ideal 134 and the model 150, in which the segmentation based on the identified ridges and edges, as shown at step 607. The result is an stl file in the CAD system 140. It should be noted that the augmentations may generally be performed by the modeling system 120 or by the CAD system 140 to the stl file, as various features may be better implemented on one system or the other.

The modified design is exported as an stl file to a 3D printer for manufacturing. The CAD system 140 generates the stl file representing the replacement image; as disclosed at step 608. A biocompatible material responsive to a 3d printer for additive manufacturing is identified, as depicted at step 609, and the 3D printer 160 fabricates the prosthetic surgical appliance 164 from rendering the replacement image from the identified bio-compatible material, as shown at step 610.

The disclosed approach may also take the form of a system or apparatus for fabricating a prosthetic appliance, including interfaces to scan devices, rendering devices, visual devices and editing devices for exchanging information pertaining to the fabricated prosthetic device. The apparatus may include an interface to a scan device for identifying a compromised skeletal structure, in which the interface is adapted to receive a scan of a contralateral anatomical structure corresponding to the compromised skeletal structure. An image processor may take the form of a computer or workstation for inverting the received scan to form a model for replacement of the compromised skeletal structure, the image processor adapted to generate, based on the model and an anatomical ideal of the compromised skeletal structure, a replacement image of a prosthetic appliance. A 3D rendering device may be fulfilled by a 3D printer or additive manufacturing facility operable to fabricate the prosthetic appliance using a biocompatible material from additive manufacturing based on the replacement image.

Those skilled in the art should readily appreciate that the programs and methods defined herein are deliverable to a user processing and rendering device in many forms, including but not limited to a) information permanently stored on non-writeable storage media such as ROM devices, b) information alterably stored on writable non-transitory storage media such as floppy disks, magnetic tapes, CDs, RAM devices, and other magnetic and optical media, or c) information conveyed to a computer through communication media, as in an electronic network such as the Internet or telephone modem lines. The operations and methods may be implemented in a software executable object or as a set of encoded instructions for execution by a processor responsive to the instructions. Alternatively, the operations and methods disclosed herein may be embodied in whole or in part using hardware components, such as Application Specific Integrated Circuits (ASICs), Field Programmable Gate Arrays (FPGAs), state machines, controllers or other hardware components or devices, or a combination of hardware, software, and firmware components.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A method of fabricating a prosthetic appliance, comprising:
    determining that a solid homogenous bone structure of a patient wrist is a compromised skeletal structure;
    receiving a contralateral scan of a contralateral anatomical structure corresponding to the compromised skeletal structure, further including:
        analyzing a series of 2-dimensional (2D) scans of the contralateral anatomic structure;
        reconstructing the 2D scans into a 3-dimensional (3D) image; and
        post-processing the 3D image into a contralateral model defining a contralateral replacement for the compromised skeletal structure;
    transposing the contralateral model to form a replacement model of the compromised skeletal structure;
    generating, based on the replacement model and an anatomical ideal of the compromised skeletal structure, a replacement image of a prosthetic appliance for a solid homogeneous wrist bone structure including a prosthetic representation of one or more of a trapezium, lunate or scaphoid bone, generating the replacement image further comprising:
        segmenting the series of 2D scans to extract portions of the contralateral anatomic structure and omit adjacent anatomic features from the fabricated prosthetic appliance; and
        transposing and interpolating the 3D image of the contralateral anatomic structure on the opposed side to invert the 3D image to correspond to the compromised skeletal structure;
        decomposing the contralateral model of the solid homogeneous bone structure into a series of contiguous spatial segments defining the compromised skeletal structure;
        receiving features of the anatomic ideal, the features including volumetric, surface and landmark features for extracting only features corresponding to the ailing skeletal feature and omitting surrounding connective tissue;
        for each of the contiguous spatial segments adjacent a corresponding cooperative structure defined by another of the trapezium, lunate or scaphoid bone:
            comparing the features of the selected spatial segment to corresponding features of the compromised skeletal structure; and
            augmenting the replacement model of the compromised skeletal structure based on deviations in the compared features by;
            determining if a corresponding healthy segment of the replacement model is available, and if so,
                selecting a corresponding spatial segment from the contralateral model using the corresponding replacement model, and if a corresponding healthy segment of the replacement model is not available,
                selecting the corresponding spatial segment from the anatomic ideal; and
                identifying corresponding ridges and edges between the anatomic ideal and the replacement model;
        assembling the selected spatial segments into the replacement image; and
    fabricating the prosthetic appliance using a biocompatible material from additive manufacturing based on the replacement image.

2. The method of claim 1 further comprising:
    forming a volumetric apportionment of the anatomic ideal and the model, the volumetric apportionment based on a segmentation of volume portions; and
    mapping corresponding volume portions between the anatomic ideal and the model, the segmentation based on the identified ridges and edges.

3. The method of claim 1 further comprising
    identifying corresponding surfaces between the anatomic ideal and the model;
    identifying surface aberrations in the model corresponding to deficiencies in the contralateral anatomical structure that should not be transferred to the fabricated prosthetic appliance; and
    omitting the identified aberrations from the fabricated prosthetic appliance.

4. The method of claim 3 further comprising computing the location of deficiencies including arthritis, fractures and necrosis in the compromised skeletal structure.

5. The method of claim 1 further comprising:
    receiving locations of structural enhancements to the prosthetic appliance, the structural enhancements including apertures adapted to receive attachment members for surgical engagement of the prosthetic appliance, the apertures including screw holes and suture holes.

6. The method of claim 1 further comprising:
analyzing a CAT (computerized axial tomography) scan of the contralateral anatomic structure;
reconstructing a series of 2D images from the CAT scan into a 3D model; and
inverting the 3D model into the model for replacement.

7. The method of claim 6 further comprising
generating an STL (stereolithography) file representing the replacement image;
identifying a biocompatible material responsive to a 3d printer for additive manufacturing;
rendering a prosthetic surgical appliance from rendering the replacement image from the identified bio-compatible material.

8. A computer program product on a non-transitory computer readable storage medium having instructions that, when executed by a processor, perform a method of fabricating a prosthetic appliance for a patient wrist, comprising:
determining that a solid homogenous bone structure is a compromised skeletal structure;
receiving a contralateral scan of a contralateral anatomical structure corresponding to the compromised skeletal structure, further including:
analyzing a series of 2-dimensional (2D) scans of the contralateral anatomic structure;
reconstructing the 2D scans into a 3-dimensional (3D) image; and
post-processing the 3D image into a contralateral model defining a contralateral replacement for the compromised skeletal structure;
transposing the contralateral model to form a replacement model of the compromised skeletal structure;
generating, based on the replacement model and an anatomical ideal of the compromised skeletal structure, a replacement image of a prosthetic appliance for a solid homogeneous wrist bone structure including a prosthetic representation of one or more of a trapezium, lunate or scaphoid bone, generating the replacement image further comprising:
segmenting the series of 2D scans to extract portions of the contralateral anatomic structure and omit adjacent anatomic features from the fabricated prosthetic appliance; and
transposing and interpolating the 3D image of the contralateral anatomic structure on the opposed side to invert the 3D image to correspond to the compromised skeletal structure;
decomposing the contralateral model of the solid homogeneous bone structure into a series of contiguous spatial segments defining the compromised skeletal structure;
receiving features of the anatomic ideal, the features including volumetric, surface and landmark features for extracting only features corresponding to the ailing skeletal feature and omitting surrounding connective tissue;
for each of the contiguous spatial segments adjacent a corresponding cooperative structure defined by another of the trapezium, lunate or scaphoid bone:
comparing the features of the selected spatial segment to corresponding features of the compromised skeletal structure; and
augmenting the replacement model of the compromised skeletal structure based on deviations in the compared features by:
determining if a corresponding healthy segment of the replacement model is available, and if so
selecting a corresponding spatial segment from the contralateral model using the corresponding replacement model and if a corresponding healthy segment of the replacement model is not available,
selecting the corresponding spatial segment from the anatomic ideal; and
identifying corresponding ridges and edges between the anatomic ideal and the replacement model;
assembling the selected spatial segments into the replacement image; and
fabricating the prosthetic appliance for surgical implantation using a biocompatible material from additive manufacturing based on the replacement image.

9. The method of claim 1 further comprising generating the 3D image and fabricating the prosthetic appliance based on apertures for securing the prosthetic appliance to adjacent skeletal structures.

10. The method of claim 1 further comprising:
generating an initial replacement image from the contralateral scan
identifying segments indicative of the compromised skeletal structure;
removing the identified segments from the initial replacement image to result in a replacement image with healthy skeletal structures remaining; and
replacing the removed segments with the corresponding spatial segment.

11. the method of claim 1 wherein the cooperative structure is based on a bone to bone interface.

12. The method of claim 1, wherein the replaced segments correspond to a contact region of an articulated bone surface with the adjacent skeletal structure.

* * * * *